United States Patent
Msika et al.

(10) Patent No.: US 9,422,504 B2
(45) Date of Patent: Aug. 23, 2016

(54) USE OF WHOLE SOFT AVOCADOS FOR PREPARING AVOCADO OIL RICH IN UNSAPONIFIABLES

(71) Applicant: LABORATOIRES EXPANSCIENCE, Courbevoie (FR)

(72) Inventors: Philippe Msika, Versailles (FR); Jacques Legrand, Neuilly sur Eure (FR)

(73) Assignee: Laboratoires Expanscience, Courbevoie (FR)

( * ) Notice: Subject to any disclaimer, the term of this patent is extended or adjusted under 35 U.S.C. 154(b) by 8 days.

(21) Appl. No.: 14/368,895

(22) PCT Filed: Dec. 26, 2012

(86) PCT No.: PCT/EP2012/076903
§ 371 (c)(1),
(2) Date: Jun. 26, 2014

(87) PCT Pub. No.: WO2013/098293
PCT Pub. Date: Jul. 4, 2013

(65) Prior Publication Data
US 2014/0357879 A1    Dec. 4, 2014

(30) Foreign Application Priority Data

Dec. 26, 2011  (FR) ...................................... 11 62461

(51) Int. Cl.
| | |
|---|---|
| C11B 1/00 | (2006.01) |
| C11B 1/06 | (2006.01) |
| A23L 1/30 | (2006.01) |
| A61K 36/54 | (2006.01) |
| C11B 1/04 | (2006.01) |
| C11B 1/10 | (2006.01) |
| C11B 1/08 | (2006.01) |
| A23L 1/212 | (2006.01) |

(52) U.S. Cl.
CPC . *C11B 1/06* (2013.01); *A23L 1/212* (2013.01); *A23L 1/3002* (2013.01); *A23L 1/3006* (2013.01); *A61K 36/54* (2013.01); *C11B 1/04* (2013.01); *C11B 1/08* (2013.01); *C11B 1/10* (2013.01); *C11B 1/102* (2013.01)

(58) Field of Classification Search
CPC .............. C11B 1/06; C11B 1/04; C11B 1/08; C11B 1/10; C11B 1/102; A23L 1/212; A23L 1/3002; A23L 1/3006; A61K 36/54
USPC ........................................................... 554/8
See application file for complete search history.

(56) References Cited

U.S. PATENT DOCUMENTS

| | | |
|---|---|---|
| 6,582,688 B1 | 6/2003 | Broutin et al. |
| 2004/0018258 A1 | 1/2004 | Piccirilli et al. |
| 2006/0099323 A1 | 5/2006 | Piccirilli et al. |

FOREIGN PATENT DOCUMENTS

| | | | |
|---|---|---|---|
| FR | 2798667 A1 | 3/2001 | |
| WO | 2004012496 A2 | 2/2004 | |
| WO | WO 2004012496 A2 * | 2/2004 | ............ A23L 1/3002 |
| WO | 2010026595 A2 | 3/2010 | |

OTHER PUBLICATIONS

Bizimana V: "Extraction, characterization, and prediction of the oxidative stability of avocado oil ", Dissertation, 1997 , pp. 1-241.*
Lee et al., Heptadecanols from the leaves of *Persea americana* var. americana, journal, Food Chemistry, 2011, pp. 921-924, Elsevier Ltd., Taiwan.
Gutfinger et al., Studies of Unsaponifiables in Several Vegetable Oils, Journal, May 13, 1974, pp. 658-663, Lipids, vol. 9, No. 9, Department of Food Engineering and Biotechnology, Haifa, Israel.
Brown, Isolation of unpleasant flavor compounds in the avocado (*Persea americana*), Journal of Agricultural and Food Chemistry, vol. 20, No. 4, pp. 753-757, 1972.
Bizimana, Extraction, characterization, and prediction of the oxidative stability of avocado oil, Dissertation, 1997, pp. 1-241, University of Minnesota.
Mostert, Characterization of micro-components of avocado oil extracted with supercritical carbon dioxide and their effect on its oxidative stability, thesis, Apr. 15, 2008, pp. 1-204, University of Pretoria.

(Continued)

*Primary Examiner* — Deborah D Carr
(74) *Attorney, Agent, or Firm* — Banner & Witcoff, Ltd.

(57) ABSTRACT

The present invention relates to the use of whole soft avocados to obtain an avocado oil rich in unsaponifiable, said unsaponifiable containing aliphatic acetogenins and/or their derivatives. Advantageously, the oil has an acid value less than or equal to 3 mgKOH/g. The invention also relates to a process for obtaining an avocado oil rich in unsaponifiable from whole soft avocados. said unsaponifiable containing aliphatic acetogenins and/or their derivatives. The invention also relates to an avocado oil rich in unsaponifiable obtainable by this process. The invention also relates to the use of the avocado oil to prepare a concentrate of avocado oil enriched in unsaponifiable or an avocado unsaponifiable rich in aliphatic furans. Finally, the invention relates to an avocado unsaponifiable rich in aliphatic furans or a concentrate of avocado oil enriched in unsaponifiable, obtainable from said avocado oil, for its use as a drug, advantageously in the prevention and/or the treatment of connective tissue disorders such as arthrosis, articular pathologies such as rhumatisms, or parodontal disorders, such as gingivitis or parodontitis.

21 Claims, No Drawings

(56) References Cited

OTHER PUBLICATIONS

Kashman et al., New compounds from avocado pear, Tetrahedron, Elsevier Science Publishers, Jan. 1, 1969, pp. 4617-4631, vol. 25, No. 18, Amsterdam, NL.

Nahrungsfette and Ole, [Extract] Ed-Bockisch, M (Jan. 1, 1993), Nahrungsfette Und—Ole, Stuttgart Ulmer De, pp. 73, 82, 175-177.

Werman et al., Avocado oil production and chemical characteristics, Journal of the American Oil Chemists Society, vol. 64, No. 1, (Feb. 1, 1987), pp. 229-232, Israel.

Anonymous, ASU Expanscience—Cutting Edge Technology to produce a unique and original ASU, (Feb. 13, 2010), pp. 1-5.

Mar. 21, 2013—(WO) International Search Report and Written Opinion—App PCT/EP2012/076903.

International Search Report dated Mar. 21, 2013 (PCT/EP2012/076903); ISA/EP.

anonymous: "ASU Expanscience—Cutting Edge Technology to produce a unique and original ASU" Feb. 13, 2010, pp. 1-5, XP002674953, Retrieved from the Internet: URL:http://web.archive.org/web/20100213004455/ http://www.original-asu.com/Cutting Edge_Technology.html [retrieved on Apr. 25, 2012] the whole document.

M. J. Werman et al: "Avocado oil production and chemical characteristics", Journal of the American Oil Chemists' Society, vol. 64. No. 2, Feb. 1, 1987, pp. 229-232, XP055025527, ISSN: 0003-021X, DOI: 10.1007/BF02542007 the whole document.

"Nahrungsfette and Ole—[Extract] Ed—Bockisch M" Jan. 1, 1993, Nahrungsfette Und Ole, Stuttgart, Ulmer, DE, pp. 7382,175-177, XP009158090, ISBN: 978-3-8001-5817-1, the whole document.

Kashman Y et al: "New compounds from avocado pear", Tetrahedron, Elsevier Science Publishers, Amsterdam, NL, vol. 25, No. 18, Jan. 1, 1969, pp. 4617-4631, XP002090295, ISSN: 0040-4020, DOI: 10.1016/S0040-4020(01)83005-2 the whole document.

Brian I. Brown: "Isolation of unpleasant flavor compounds in the avocado (*Persea americana*)", Journal of Agricultural and Food Chemistry, vol. 20. No. 4, Jul. 1, 1972, pp. 753-757, XP055025721, ISSN: 0021-8561. DOI: 10.1021/jf60182a019 the whole document.

Gutfinger T et al: "Studies of unsaponifiables in several vegetable oils", Lipids, Springer, US, vol. 9, No. 9, Jan. 1, 1974, pp. 658-663, XP009158777, ISSN: 0024-4201, DOI: 10/1007/BF02532171 tables I-IV.

Tzong-Huei Lee et al: "Heptadecanols from the leaves of *Persea americana* var. americana", Food Chemistry, vol. 132, No. 2, Nov. 19, 2011, pp. 921-924, XP055025945, ISSN: 0308-8146, DOI: 10.1016/j.foodchem.2011.11.067 the whole document.

Mostert, Mathilda Elizabeth: "Characterization of micro-components of avocado oil extracted with supercritical carbon dioxide and their effect on its oxidative stability", Apr. 15, 2008, XP002675113, Retrieved from the Internet: URL:http://upetd.up.ac.za/thesis/available/etd-06062008-1324061 [retrieved on May 2, 2012] pp. sans numerotation: 1-10; pp. i-x; pp. 1-183 the whole document.

Bizimana V: "Extraction, characterization. And prediction of the oxidative stability of avocado oil", Dissertation. 1997, pp. 1-241, XP009158924, University of Minnesota the whole document.

\* cited by examiner

USE OF WHOLE SOFT AVOCADOS FOR PREPARING AVOCADO OIL RICH IN UNSAPONIFIABLES

The present application is a U.S. National Phase filing of International Application No. PCT/EP2012/076903 filed on Dec. 26, 2012, designating the United States of America and claiming priority to French Patent Application No. 1162461, filed on Dec. 26, 2011; and the present application claims priority to and the benefit of both of the above-identified applications, both of which are incorporated by reference herein in their entireties.

The present invention relates to the use of whole soft avocados to obtain an avocado oil rich in unsaponifiable. Advantageously, said unsaponifiable contains aliphatic acetogenins and/or their derivatives. In particular, said oil has a low acid value, typically less than or equal to 3 mgKOH/g. The invention also relates to a process for obtaining avocado oil rich in unsaponifiable from whole soft avocados, advantageously said unsaponifiable containing aliphatic acetogenins and/or their derivatives. The invention also relates to avocado oil rich in unsaponifiable obtainable by said process. The invention also relates to the use of the avocado oil to prepare a concentrate of avocado oil enriched in unsaponifiable or an avocado unsaponifiable rich in aliphatic furans. Finally, the invention relates to an avocado unsaponifiable rich in aliphatic furans or a concentrate of avocado oil enriched in unsaponifiable, said unsaponifiable or said concentrate being obtainable from said avocado oil, for its use as a drug, advantageously in the prevention and/or the treatment of connective tissue disorders such as arthrosis, articular pathologies such as rhumatisms, or parodontal disorders, such as gingivitis or parodontitis.

Due to the increase in its cultivated areas, its accessibility throughout the year worldwide, the augmentation of the GDP per capita, its food interest and its nutritional values, consumption of avocado tends to be generalised worldwide. The avocado market is therefore mainly based on the sale of the fruit for use in the alimentation either of the fruit directly, or of its derivative products, such as guacamole or its oil.

The growth of world commerce in avocado confirms the growing interest for this fruit and its value, in particular due to its nutritional benefits i.e. for health. So, this world market is based on massive export from producing countries and strong demand from importing countries, causing a relatively high price level of this raw material.

However, industrial production of avocado and its international commerce must consider the particular physiological characteristics of this fruit which make it sensitive to storage and conservation.

Therefore, managing the fruits after harvesting, the latter dependent on market fluctuations of this direct-consumption fruit is a primordial factor which directly influences the production yield of farmers (samples and blossoming) and the control of their losses.

During its development and its maturation, the avocado passes through several stages which correspond to the different physiological phases of its evolution on the tree and during its harvesting through to its conservation.

Therefore, during its life on the tree, the fruit undergoes a growth phase, then maturation to finally reach senescence.

During the growth period of the fruit, the plant accumulates substances, such as proteins, lipids or starch, the latter two being assimilable in substances known as carbonated reserves. These substances serve to ensure the continuity of metabolism after harvesting. These reserves are then metabolised as a function of storage conditions and time, and this more or less rapidly.

The physiological maturity of the fruit corresponds to a life period during which natural processes are conducted which complete the biometric growth of the fruit.

The maturation of the fruits corresponds to a set of biochemical and physiological changes leading to the state of maturity and giving the fruit its chemical and organoleptic characteristics, such as aroma, colour, hardness which gives the fruit its marketable and comestible character.

Of the biochemical changes the fruit undergoes, some are visible, such as the degradation of chlorophylls during maturation which are resorbed by progressively showing other pigments. The colour of the fruit comes from pigments localised in the cytoplasm or in the cellular vacuoles.

One of the important changes associated with the evolution of the fruit is its loss of firmness. This transformation is besides attributed to degradation inter alia of pectic substances, support molecules of the cellulose. It is characterised mainly by progressive decomposition of the cellular wall causing slackening of the cellulosic fibres and leading to loss in rigidity and firmness of the fruit. It is the result of specific enzymatic actions, especially represented by cellulases and polygalacturonases. This modification of the internal structure of the fruit facilitates cellular exchanges between the different organs of the fruit and also causes release and diffusion of the oil. Beyond the state of maturity, the fruit enters a senescence phase leading to biological and physiological modification, followed by cellular disorganisation i.e. catabolism. During these different phases, the composition of the avocado is modified. In particular, variations in its water, oil, unsaponifiable and free fatty acid content are observed.

When these fruits come onto the market, they often no longer have any degree of firmness while their softening process has already started. The market time of the fruits is then limited over time.

The extraction of the oil from this fruit rich in lipids has appeared rapidly as a possible use of this plant, especially for the valorisation of commercial stocks not exploitable on the food market, which can be qualified as by-products of the avocado sector.

Using such fruits for the production of avocado oil limits the choice of processes and technologies to be implemented. Therefore, the quality and the maturity stage are important factors for the preparation of avocado oil and will shape the choice of the process which will be used to produce this oil, the quality and the composition of the oil produced, especially at the level of its acidity, content and composition of its unsaponifiable.

Different methods for extraction of the oil from fruits have been developed, examples of which are extraction techniques by centrifuging, by pressure or by extraction by means of solvents. The quality of the fruits used, their preparation, the technologies used, the triturating conditions and those of conservation considerably impact the quality of the oil produced, its composition, its extraction yield, its properties and, as a consequence, its use.

The production process of avocado oil mainly used today utilises the extraction technology by centrifuging. The avocados, stripped of their skin and their kernel, are ground and mixed with addition of water. Two separation steps by centrifuging are then necessary to isolate the oil. The quality of the oil obtained by this process depends mainly on the quality of the fruits used, essentially associated with their level of maturity and softening approaching senescence: this condition causes a high acid value because of the use of a large quantity of water and the activation of native lipases of the fruit due to cellular decompartmentation and the presence of free water and/or its emulsion in presence of the oil.

In addition, this process which appears very interesting to prepare an avocado oil intended for food or cosmetic applications has a major defect for other applications: such a process is selective and does not extract the full potential in unsaponifiable present in the fruit. In particular, the polar compounds of the unsaponifiable, such as aliphatic acetogenins of fatty polyhydroxy alcohols or persin type, which are precursors of aliphatic furans, are not extractible from the fruit by this process. In fact, the relatively stable bonds by which they are fixed within the matrix of the fruit cannot be broken by this type of process.

Processes based on pressing of the fresh pulp with the aid of third-party products (plant silica . . . ) or steam have also been developed, but they too do not result in an oil quality rich in unsaponifiable.

Processes integrating drying fruits at low temperature (lyophilisation) before extraction have also been used. However, these processes, even if they include an extraction step, for example by pressure or extraction by solvent, do not lead to preparation of oil rich in aliphatic acetogenins of persin type and therefore result in oil with relatively low unsaponifiable content and mainly constituted by sterols.

More generally, processes from fresh or previously dehydrated avocados have been developed which integrate the use of solvents of specific polarities. These processes aim to prepare avocado oils or extract active constituents from the avocado for cosmetic, food, nutraceutical or pharmaceutical applications. However, with respect to their industrial development, the toxicity and chemical stability of the solvent or solvents used, as well as from an economic and environmental viewpoint, the viability of these processes is still in question.

In addition, preparation processes of avocado oil by drying at higher temperature and by pressing dehydrated avocados are not directly applicable to soft avocados because of mechanical properties of this quality of fruits. In fact, soft fruits are not suitable for usual conditions of slicing and drying operations usually used. For the skilled person, it was not either likely or obvious at all that soft and pasty, moist, semi-dried or dried organic products, could be treated by the extraction technology of the oil by pressure.

On the other hand, economic demands associated with the high retail price of avocado oil compel acquisition of perfect control over pressing yields and obtaining technical reliability of the industrial process used.

Therefore, there was a need to develop a novel process for obtaining quality oil from soft fruit which constitutes by-products of edible avocado, in particular with a good yield while optimising their unsaponifiable potential.

Also, demands for processes developed for extracting the unsaponifiable from avocado oils, especially those integrating a step for concentration of the unsaponifiable fraction by molecular distillation, impose the use of oil having a low acid value.

The present invention aims to bridge this need. The applicant has discovered a novel process for obtaining quality oil from soft avocados with a satisfactory yield while leading to obtaining a high unsaponifiable content, by extracting the polar compounds such as aliphatic acetogenins, by limiting the action of enzymes of lipase type, in particular by limiting, or even eliminating, hydrolysis of glycerides such as triglycerides of the oil, and having a low acid value. The process according to the present invention therefore produces oil having a high content in aliphatic acetogenins and their derivatives.

In addition, the process according to the present invention produces, with high yield, an avocado oil rich in unsaponifiable, which can advantageously be incorporated into cosmetic, dermatological, pharmaceutical compositions or medical devices, or even in food compositions, food or nutraceutical supplements, for human or animal consumption.

Also, from the oil according to the present invention, an avocado unsaponifiable rich in aliphatic furans can advantageously be extracted which in turn can be incorporated into cosmetic, dermatological, pharmaceutical compositions or medical devices, or even in food compositions, food or nutraceutical supplements, for human or animal consumption.

The aim of the present invention is the use of whole soft avocados to obtain an avocado oil rich in unsaponifiable, said unsaponifiable containing aliphatic acetogenins and/or their derivatives, in which the unsaponifiable content of the oil is at least 3% by mass, relative to the total mass of the oil, and the content of aliphatic acetogenins and/or their derivatives of the oil is at least 2% by mass, relative to the total mass of the oil.

In particular, the aim of the present invention is the use of whole soft avocados to obtain an avocado oil by mechanical pressure containing at least 3% of unsaponifiable mass relative to the total mass of the oil, said unsaponifiable containing aliphatic acetogenins and/or their derivatives, in which the content of aliphatic acetogenins and/or their derivatives of the oil is at least 2% m/m, the soft avocados having a penetration resistance force in the flesh less than or equal to 3 $kg/cm^2$, said penetration resistance force being measured by means of a penetrometer.

The majority of varieties of avocado can be used within the scope of the present invention to produce oil with the preferred characteristics, to the extent where they include the qualitative and quantitative potential of specific compounds.

Particularly advantageously, the process according to the invention is applied to the most commonly grown varieties and representing the quasi totality of tonnages exported and marketed on a world level, preferably the hass and fuerte varieties.

In the sense of the present invention, the term « whole » avocados means avocados containing the skin, the pulp and the kernel distributed in their entirety.

Typically, soft avocados according to the invention have a degree of softening equivalent to that of immediate consumption of the avocado, and exclude the eventuality of a mechanical pre-treatment by slicing.

Advantageously according to the present invention, soft avocados are characterised by the firmness of their flesh measured by means of a penetrometer and defined by a penetration resistance force. Particularly advantageously, the soft avocados have a penetration resistance force in the flesh less than or equal to 3 $kg/cm^2$, typically less than or equal to 2 $kg/cm^2$, for example less than or equal to 1 $kg/cm^2$.

Typically, according to the present invention, the penetration force is measured by means of a penetrometer of PCE-PTR 200 or FT 327 type, which measures the kilogram force necessary to have a calibrated nozzle penetrate the fruit. Advantageously, the fruit is peeled before the measurement is taken to dispense with the resistance of the skin (tegument) and the variability related to the different varieties of avocado tested. The rod, also called pointal or nozzle used for this measurement has a nominal diameter of the order of 6 to 11.3 mm.

Advantageously, the oil obtained according to the present invention is rich in unsaponifiable. The term « rich in unsaponifiable » means oil which typically contains at least 3% of unsaponifiable mass, advantageously at least 5% of unsaponifiable mass, relative to the total mass of the oil. For example, the oil contains between 3 and 12% of unsaponifiable mass, in particular 5 to 12%, more particularly 8 to 12%, by mass of unsaponifiable, relative to the total mass of the oil.

The unsaponifiable comprises all the constituents of a fatty body which after saponification in a strongly alkaline medium are not very soluble or insoluble in water, and soluble in organic solvents such as ethyl ether, aromatic hydrocarbons, chlorinated solvents . . . .

The unsaponifiable is therefore composed of all the non-hydrolysable constituents of the fatty body, as well as those resulting mainly from the saponification of non-glyceride esters of fatty acids (sterol esters, waxes, tocopherol esters . . . ).

Four major groups or families of substances are generally present in the majority of unsaponifiables of plant oils. The most important group by mass is represented by that which resembles sterols including pentacyclic triterpenic alcohols and 4-methyl sterols. The second group is constituted by tocopherols which can integrate tocotrienols. The two other groups are aliphatic alcohols and saturated and unsaturated aliphatic hydrocarbons.

The composition of the avocado unsaponifiable differs from the composition conventionally found in plant oils since it mainly integrates specific constituents of the avocado.

The majority fraction of the avocado unsaponifiable is represented by the group of aliphatic furans. The second family of molecules combines fatty polyhydroxy alcohols. The third group is constituted by sterols including pentacyclic triterpenic alcohols and 4-methyl sterols. The other groups are minorities.

The unsaponifiable contained in the oil according to the invention advantageously contains aliphatic acetogenins and/or their derivatives.

Within the scope of the invention, aliphatic acetogenins and their derivatives are especially fatty polyhydroxy alcohols and their acetylated derivatives, and/or 1,2-dihydroxy-4-oxo-aliphatic alcohols and their acetylated derivatives of « persin» type, and/or aliphatic furans, as well as their mixtures.

The fatty polyhydroxy alcohols are also called Fraction I. These are especially triols of the long-chain acetylenic and olefinic 1,2,4-trihydroxy type. The acetylated derivatives of the fatty polyhydroxy alcohols are typically in position 1, 2 or 4.

The 1,2-dihydroxy-4-oxo-aliphatic alcohols are also called persin, and are precursors of the Fraction H. These are especially ketone diols of long-chain acetylenic and olefinic 1-2-dihydroxy-4-oxo type. The acetylated derivatives of these compounds are typically in position 1.

Persins are typically found in the idioblasts, oleaginous cells in the case of the avocado.

For example, persin of the following structure molecular can be cited in particular:

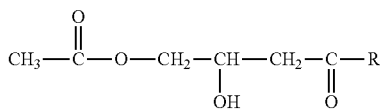

Aliphatic furans are also called furanic lipids, or more commonly avocado furans or Fraction H. These are especially derivatives of persin comprising a furan grouping, which result in particular from the chemical transformation by dehydration and intramolecular cyclisation of persin extracted from the avocado. By way of example, 2-alkyl furans can be cited.

Advantageously, the unsaponifiable of the oil according to the present invention is rich in aliphatic acetogenins and/or their derivatives. Particularly advantageously, the oil typically contains at least 2% by mass of aliphatic acetogenins and/or of their derivatives, typically at least 3% by mass of aliphatic acetogenins and/or of their derivatives, relative to the total mass of the oil. For example, the oil contains between 2 and 10%, in particular between 3 and 10%, more particularly between 5 and 8% by mass of aliphatic acetogenins and/or of their derivatives, relative to the total mass of the oil.

In a particular embodiment according to the present invention, the oil contains at least 3% of unsaponifiable mass, relative to the total mass of the oil, and contains at least 2% by mass of aliphatic acetogenins and/or of their derivatives, relative to the total mass of the oil.

In another particular embodiment according to the present invention, the oil contains at least 5% of unsaponifiable mass, relative to the total mass of the oil, and contains at least 3% by mass of aliphatic acetogenins and/or of their derivatives, relative to the total mass of the oil.

Typically, the unsaponifiable of the oil according to the invention contains sterols. For example, β-sitosterol can be found as mainly representing 4-desmethysterols, citrostadienol for the family of 4-monomethylsterols, and/or 24-methylene cycloartenol for the family of 4,4-dimethylsterols.

According to a particular characteristic of the invention, the oil contains at least 0.5% by mass of sterols, advantageously at least 0.8% by mass of sterols, relative to the total mass of oil.

Particularly advantageously according to the invention, the whole soft avocados are ground, then dried at high temperature, typically between 60 and 150° C., advantageously to obtain a residual humidity less than or equal to 5%, before obtaining oil by mechanical pressure.

According to a particular characteristic according to the present invention, following grounding and drying the avocados, 1 to 5% of water or water vapour relative to the mass of ground dry avocados, are added before obtaining oil by mechanical pressure.

It has actually been discovered that when a water or water vapour injection step is integrated into the dried avocados, this produces avocado oil rich in unsaponifiable with a high yield.

Particularly advantageously, the oil according to the invention has a low acid value, generally less than or equal to 5 mgKOH/g, advantageously less than or equal to 3 mgKOH/g, typically less than or equal to 1 mgKOH/g.

Another aim of the present invention is a process for obtaining avocado oil rich in unsaponifiable from whole soft avocados, in which said unsaponifiable contains aliphatic acetogenins and/or their derivatives, comprising at least the following successive steps:

Grinding of the soft avocados, resulting advantageously in obtaining a ground product granulometry of between 2 and 20 mm, in particular between 2 and 10 mm, Drying of the ground product at high temperature, advantageously at a temperature between 60 and 150° C., in particular between 65 and 120° C., for example between 70 and 100° C., typically between 80 and 100° C., Extraction of the oil advantageously by mechanical pressure (1) In particular, an aim of the present invention is a process for obtaining avocado oil from whole soft avocados, said oil containing at least 3% of unsaponifiable in mass relative to the oil total mass, in which said unsaponifiable contains aliphatic acetogenins and/or their derivatives, comprising the following successive steps: Grinding of the soft avocados, resulting in obtaining a ground product granulometry of between 2 and 20 mm, in particular between 2 and 10 mm, (2) Drying of the ground product at high temperature, advantageously at a temperature between 60 and 150° C., in particular between 65 and 120° C., for example between 70 and 100° C., typically between 80 and 100° C., to obtain a residual humidity less than or equal to 5%.

(3) Adding water to the dried avocados by addition of 1 to 5% of water or water vapour relative to the mass of ground dry avocados, then advantageously homogenisation by blending, before introduction to the press, then.

(4) Extraction of the oil by mechanical pressure.

It has been discovered that the soft fruit was unable to lend itself to the usual conditions of slicing or drying operations performed on hard avocados.

In fact, due to the constitution in three distinct parts of the fruit, the skin, the pulp and the kernel, its behaviour during slicing will be highly variable as a function of its degree of maturity and firmness of the pulp and of the skin. In the first phase following its harvesting, the fruit has a homogeneity of structure and hardness between the three parts, favourable to its slicing. As soon as the pulp starts to soften, the compartmental hardness of the fruit (pulp, skin, kernel) becomes very heterogeneous and prevents any industrial slicing sue to the presence of the kernel which remains very hard and the loss of consistency of the skin and of the pulp.

In addition, it has been discovered that drying soft fruit represented a major obstacle to implementing processes known to the man skilled in the art to extract avocado oil rich in its unsaponifiable fraction.

The drying of the whole soft fruit without preparation does not yield satisfactory results, as it produces heterogeneous drying in residual free water favourable to the appearance of parasite and heterogeneous reactions, degradation factors of the oil and its unsaponifiable.

The grinding and the drying of the soft fruit in uncontrolled conditions results in the same phenomena and production of oil highly variable in quality, limiting or penalising its uses.

The present invention proposes a solution for the preparation, possible conditioning, and drying of soft avocados, guaranteeing preparation of quality avocado oil. This oil is especially characterised by a low acid value, a high unsaponifiable content and a composition particular to this unsaponifiable.

Within the scope of the present invention, soft avocados advantageously undergo a first grinding step (1). This step effectively breaks up the different parts of the soft avocado.

In a particular embodiment according to the present invention, the grinding (1) is done on the whole avocados constituted by the skin, the pulp and the kernel. The grinding (1) advantageously shreds the skin, softens the kernel and blends the mixture to obtain a homogeneous dispersion and granulometry of the ground product (resulting particles and pieces) in the avocado pulp.

Typically, the grinders used are adapted to the very big difference in size, texture and hardness of the different parts which make up the avocado: skin, pulp and kernel. Therefore, the grinder technology to be employed must process materials having very hard parts (kernel) and tenderer parts (skin), or even very soft parts (pulp).

The grinding (1) is advantageously done by means of a grinder of serrated knives or rollers type.

The configuration and adjustment must however be generally adapted as a function of the size of the fruits, their maturity and their quality (kernel, pulp and skin biometry) to result in the advantageously preferred granulometry.

In another particular embodiment according to the present invention, the grinding (1) is preceded by a previous separation step of the different parts of the soft fruit before grinding. Effective technologies exist for separating the kernels and the skin from the pulp of the avocado. These different parts can be processed independently by grinding on adapted equipment before being remixed then dried.

Typically, soft avocados are processed first on a machine of purifying type which produces pulp from one side and the kernels and skin from the other side.

Generally, the skin and kernel mixture is then ground in a grinder of the knife grinder type or all other appropriate grinders to obtain a granulometry complying with the advantageously expected specifications described especially hereinbelow.

The ground product is then remixed with the pulp in a blender and in the appropriate proportions to obtain a homogeneous mixture having regular dispersion of particles of skin and kernel in the pulp.

Therefore, typically in this embodiment, the succession of the following steps is undertaken:

Separation of the kernel and of the skin from the pulp of the avocados,

Grinding of the different parts isolated from the soft avocados, then

Blending of the different ground parts to obtain a homogeneous dispersion of the particles of skin and kernel in the pulp.

Particularly advantageously according to the invention, the grinding (1) is done in such a way as to produce a specific size of particles and pieces, responding to a granulometry range which gives the ground product a texture adapted to rapid drying. This texture is characterised by a non-continuous visual appearance, the pieces being detectable generally in the mass without use of an additional optical instrument. Typically, the surface of the ground product is not smooth and comprises roughness represented by the particles of kernel and skin. During drying, the ground product does not form a compact mass, but easily friable blocks.

More precisely, the size of the particles is advantageously selected between 2 and 20 mm, and more particularly still between 2 and 10 mm.

Advantageously according to the invention, the mixture, once ground, must be distributed in an appropriate way to ensure homogeneity of the drying (2) which follows with the greatest efficacy. Different techniques are applicable, such as blending and particular possible conditioning, such as spreading in a thin layer, depositing of the paste in even piles by means of buses or combs, formation of volumes structured by means of dies or by extrusion.

The homogenised ground product is distributed advantageously and carefully to produce during the following drying step (2) rapid evaporation of water, controlled rise in temperature of the product, homogeneous drying and minimal adherence to the drying support.

Therefore, typically, in a particular embodiment, following grinding (1) and prior to drying (2), conditioning of the ground product is carried out to increase the surface of the ground product to be dried, advantageously by spreading in a thin layer, typically to result in a film of minimal thickness advantageously of between 0.5 and 5 cm, in particular between 1 and 2 cm, or again by shaping to optimise surface evaporation of extrusion type or passing through a die.

This conditioning operation can employ different techniques, such as:

Spreading out on trays, perforated plates, drying grating or on a conveyor belt, in a film of even thickness, for example by moving between two rollers;

Deposit of «pastes» by a metering machine or passing through a die;

Extrusion;

Or any other machines adapted to produce an even structure conducive to homogeneous and reproducible drying.

The aim of the following controlled dehydration or drying step (2) of the ground product is to extract water from the medium, but also to make the polar compounds extractible from the unsaponifiable. It is carried out, in particular, by way of specific technology and at a temperature selected to optimise energy needs and limit unwanted reactions. In fact, too low a temperature would limit the evaporation speed of the water and favour the action of the lipases, causing hydrolysis of glycerides and a rise in the acid value of the medium. Too high a temperature would favour the phenomenon of crusting, as well as thermal or oxidative or non-oxidative degradation (Maillard reaction) of the fragile and reactive compounds of the unsaponifiable or unsaturated compounds of the oil.

With the aim of obtaining an oil of preferred composition, it has been discovered that it was recommended to use a drying step at a controlled temperature. The very high water content of the avocado (≈75%) requires a very efficacious and specific drying technique to guarantee rapid evaporation not causing degradation of constituents particular to the fruit.

In fact, the drying of soft avocados, without particular preparation and undertaken as is usually done in the prior art, does not result in obtaining an avocado oil of satisfactory quality. The barrier of the skin and the texture of the avocado make migration of water to the surface very difficult and limit its evaporation. Under these temperature conditions, the strongly hydrated medium inside the pulp can make the action of lipases very favourable to leading to a high acid value on the extracted oil, as well as to degradation of its unsaponifiable.

In addition, separation of the pulp by elimination of the kernel and the skin, then drying of the blended pulp in a thin layer improves drying, but does not lead to an oil with the preferred qualities. A surface crust forms during drying which blocks the evaporation process and which maintains residual humidity within the paste favourable to significant action of the lipases. The variation in thickness of the layer during drying has no significant effect on controlling this parasite reaction.

Now, very surprisingly, it has been discovered that drying the avocado, when carried out from a ground mixture including the pulp, the kernel and the skin, as is done in the present invention, leads to rapid and optimum dehydration with a very limited activity of lipases.

The use of the mixture of the three parts also contributes an important advantage during drying, as it prevents adherence of the material on the drying trays. In fact, the ground product obtained from whole avocados unsticks very easily from the trays after drying contrary to the pulp ground product which sticks to the metal and prevents rapid unloading.

It has also been discovered surprisingly that the granulometry obtained during grinding (1) significantly impacted the kinetics of drying (2) and the quality of the oil extracted.

The size of particles obtained following grinding must advantageously result in obtaining an even heterogeneous mixture which avoids the formation of a compact mass during drying which would block migration of water to the surface and limit surface evaporation.

Advantageously according to the invention, the even heterogeneous texture favours circulation of air inside the mass and improves evaporation of water. It prevents formation of a surface smooth in contact with the surface of the drying trays, limiting adherence between the two surfaces.

Particularly advantageously according to the invention, the drying (2) of the ground product is done at a controlled temperature, advantageously at a temperature between 60 and 150° C., in particular between 65 and 120° C., for example between 70 and 100° C., typically between 80 and 100° C.

According to a particular characteristic of the invention, the drying (2) of the ground product is carried out for 8 to 78 h, advantageously over 10 to 24 h.

The drying (2) according to the invention can be done in particular by drying in a hot air current or in a controlled atmosphere (ex. nitrogen), by drying at atmospheric pressure or in a vacuum, or by drying by microwave.

Within the scope of the present process, for reasons of ease of industrial implementation and for cost reasons, drying in ventilated dryers, in a thin layer and a hot air current, at a temperature between 80 and 100° C., for 8 to 72 hours is preferred.

Advantageously, on completion of drying (2), the dried ground product has a rate of residual humidity less than or equal to 5% m/m.

The residual humidity is typically measured by means of a thermogravimetric method by IR drying. Other methods can also be used, such as the method of loss to drying in heat chamber or the Karl Fischer titering method.

During drying, three successive phases are typically observed:

A phase of temperature rise of the product to the humid temperature of the drying air, A drying phase at constant speed which correspond to surface evaporation of the fruit and to migration of free water from inside the product to the periphery, A drying phase at decreasing speed during which the availability of water at the surface decreases due to the limitation of its migration speed inside the fruit. At this stage of the drying, there is no more free water, but mainly bound water much less available to evaporation. It is however particularly advantageous to lower its residual content to a maximum to stabilise the plant and block microbial developments and limit internal transformations by residual enzymatic actions. For the avocado, a residual content of 5% is typically considered the maximum.

Residual humidity less than or equal to 5% also plays an important role in the consistency of dried avocados, giving them a solid brittle texture favourable to resisting the physical stresses developed during mechanical pressing. Beyond 5% humidity, the dried avocado has a soft consistency which results, during pressing, in the formation of a purée without sufficient consistency to be pressed efficaciously.

It has been found that, even with residual humidity of less than or equal to 5% and consistency appropriate to pressure, these conditions are not totally sufficient to achieve pressing conditions for a high extraction yield of oil.

It has been discovered surprisingly that readjustment of the residual humidity (3) by addition of 1 to 5% of water or water vapour, for example from 1 to 3% of water or water vapour, relative to the mass of dry avocados, would considerably increase the extraction rate of the oil, and accordingly the efficacy of pressing.

This readjustment/water adding operation (3) must be advantageously carried out just before introduction of the dried fruits to the press by addition of purified water or water vapour so that the dry avocados become saturated in humidity in surface without losing their firm and crunchy consistency so that no softening happened.

To be efficacious, this rate of residual humidity can be obtained only by previous dehydration (2) of the avocados, then readjustment by addition of water (3). In fact, partial and controlled direct dehydration does not produce a product texture compatible with pressing, as has been pointed out earlier.

In particular according to the invention, water adding (3) in dried avocados is performed by controlled addition of water or water vapour to the dried and ground avocados, then homogenisation by blending typically in a planetary mixer, advantageously for ½ h to 1 h.

More particularly according to the invention, water adding (3) in the dried avocados is carried out continuously in a conveyor of the endless screw type. Water or water vapour is added to the avocados at the conveyor head and homogenisation occurs by agitation in the conveyor, as the product is being moved. The dimensioning of the conveyor must typically ensure a minimum dwell time of ½ h the dried avocados.

Even more particularly according to the invention, the conveyor is used to feed the extraction press.

The extraction step (4) of the oil is quite particularly advantageously preceded by a water adding step (3) in dried avocados by addition of 1 to 5%, preferably from 1 to 3%, of water or water vapour relative to the mass of dried avocados.

The extraction step (4) of the oil is advantageously completed by mechanical pressing of the dry material after water adding. Usually, to be able to work efficaciously, extraction presses must receive material containing content of fibres and adapted organic material which gives the produced oil cake a consistency which reaches high pressure at the press head indispensable to ensure an adapted pressing yield.

The extraction step (4) according to the invention is generally completed via filtration which eliminates the solid particles and guarantees the limpidity of the oil produced.

The process according to the present invention produces quality avocado oil with a particular composition, especially having a low acid value and high potential in unsaponifiable and a particular composition of this unsaponifiable.

Another aim of the present invention is avocado oil rich in unsaponifiable able to be obtained by the process according to the invention.

Advantageously, the oil contains at least 3% of unsaponifiable mass, typically at least 5% of unsaponifiable mass, relative to the total mass of the oil. For example, the oil contains between 3 and 12% of unsaponifiable mass, in particular 5 à 12%, more particularly 8 to 12%, by mass of unsaponifiable, relative to the total mass of the oil.

According to a particular characteristic of the invention, the oil contains at least 2% by mass of aliphatic acetogenins and/or of their derivatives, relative to the total mass of the oil, said aliphatic acetogenins and their derivatives being such as defined hereinabove and advantageously being fatty polyhydroxy alcohols and their acetylated derivatives, and/or 1,2-dihydroxy-4-oxo-aliphatic alcohols and their acetylated derivatives of « persin» type, and/or aliphatic furans.

Particularly advantageously, the oil typically contains at least 3% by mass of aliphatic acetogenins and/or their derivatives, relative to the total mass of the oil. For example, the oil contains between 2 and 10%, in particular between 3 and 10%, more particularly between 5 and 8% by mass of aliphatic acetogenins and/or their derivatives, relative to the total mass of the oil.

In a particular embodiment according to the present invention, the oil contains at least 3% of unsaponifiable mass, relative to the total mass of the oil, and contains at least 2% by mass of aliphatic acetogenins and/or their derivatives, relative to the total mass of the oil.

In another particular embodiment according to the present invention, the oil contains at least 5% of unsaponifiable mass, relative to the total mass of the oil, and contains at least 3% by mass of aliphatic acetogenins and/or their derivatives, relative to the total mass of the oil.

Typically, the unsaponifiable of the oil according to the invention contains sterols.

According to a particular characteristic of the invention, the oil contains at least 0.5% by mass of sterols, advantageously at least 0.8% by mass of sterols, relative to the total mass of the oil.

Particularly advantageously, the oil according to the invention has a low acid value, generally less than or equal to 5 mgKOH/g, advantageously less than or equal to 3 mgKOH/g, typically less than or equal to 1 mgKOH/g.

Another aim of the present invention is a composition containing avocado oil rich in unsaponifiable, advantageously at a concentration of between 0.1 and 99.9% by mass, still more advantageously from 30 to 70% by mass, relative to the total mass of the composition.

Another aim of the present invention is the use of the avocado oil such as defined hereinabove to prepare a concentrate of avocado oil enriched in unsaponifiable fraction.

The term concentrate of avocado oil enriched in unsaponifiable fraction means in the sense of the present invention a concentrate of avocado oil containing a high content of unsaponifiable, typically containing at least 20%, for example between 30 and 60% of unsaponifiable by mass, relative to the total mass of the concentrate.

Advantageously, the unsaponifiable of the concentrate of avocado oil according to the invention contains aliphatic acetogenins and/or their derivatives.

Another aim of the present invention is the use of the avocado oil such as defined hereinabove or of the concentrate of avocado oil such as mentioned hereinabove to prepare an avocado unsaponifiable rich in aliphatic furans.

The concentration steps of the oil in its unsaponifiable fraction to prepare a concentrate such as mentioned hereinabove, and preparation of an avocado unsaponifiable rich in aliphatic furans (furanic lipids) from the oil or the concentrate are those described hereinbelow in particular.

The preparation of the concentrate is generally done by cold crystallisation or by molecular distillation. Advantageously, the oil concentrate is prepared by molecular distillation, typically at a temperature between 180 and 260° C. and maintaining pressure of between $10^{-2}$ and $10^{-3}$ mmHg.

This molecular distillation step of the avocado oil is preferably carried out using a device selected from molecular distillers of centrifuge type and devices of scrap film type.

The preparation of the avocado unsaponifiable rich in aliphatic furans from oil or concentrate generally includes thermal treatment of the oil or concentrate at a temperature between 80 and 150° C., followed by a saponification and extraction step of the unsaponifiable, for example by means of a solvent.

Following extraction of the unsaponifiable, additional purification or fractioning can be conducted.

Another aim of the present invention is the concentrate of avocado oil enriched in unsaponifiable fraction prepared from the avocado oil according to the invention.

Another aim of the present invention is the total unsaponifiable or the unsaponifiable fraction prepared from the avocado oil according to the invention or of the concentrate of avocado oil according to the invention.

Another aim of the present invention is a composition containing an unsaponifiable prepared typically from the avocado oil according to the invention or of the concentrate such as mentioned hereinabove, typically a total unsaponifiable or an unsaponifiable fraction, advantageously at a concentration of between 0.1 and 99.9% by mass, more advantageously still from 30 to 70% by mass, relative to the total mass of the composition.

The total unsaponifiable includes all families of constituents typically present in the unsaponifiable of the original oil in question.

An unsaponifiable fraction results typically from one or more fractioning operations to produce advantageously in the form of a purified fraction a compound or a family of compounds comprising the unsaponifiable.

Advantageously, the composition according to the invention contains an avocado oil rich in unsaponifiable according to the present invention and/or a concentrate prepared typically from the oil according to the invention and/or an unsaponifiable prepared typically from the avocado oil or the concentrate according to the invention, typically a total unsaponifiable or an unsaponifiable fraction.

The composition according to the invention can also comprise other active ingredients.

Of the ingredients recommended in association with the oil and/or the concentrate and/or the unsaponifiable according to the invention, plant extracts can be cited, in particular:

- Plant oils or butters such as soya oils and/or the rapeseed oil, lupin oil, advantageously soft white lupin oil, or a mixture of these oils or butters;
- the oleodistillate or plant or animal oil concentrates, especially sunflower, more advantageously concentrates of linoleic sunflower, such as sunflower oil concentrated in unsaponifiable (Soline) marketed by Laboratoires Expanscience, oils concentrated in unsaponifiable of soya, rapeseed, maize or palm oil type;
- plant unsaponifiables or plant oil, advantageously furans of avocado (Avocadofuran), unsaponifiables of avocado and/or soya, more particularly a mixture of unsaponifiables of furanic avocado and soya unsaponifiables, advantageously in a respective ratio of around 1/3-2/3 (such as Piascledine® 300), soya unsaponifiables, sterolic unsaponifiables (typically unsaponifiables whereof the sterol content, of methyl sterols and triterpenic alcohols is between 20 and 95% by mass, preferably 45-65% by mass, relative to the total mass of the unsaponifiable), phytosterols, sterol esters and vitamin derivatives.

In particular, the composition according to the invention contains an avocado unsaponifiable according to the invention in association with a soya unsaponifiable, advantageously in a ratio of around 2/3 for the soya and 1/3 for the avocado (such as Piascledine® 300).

Finally, another aim of the present invention is avocado oil rich in unsaponifiable according to the present invention, such as described hereinabove or the concentrate of avocado such as described hereinabove or the unsaponifiable such as described hereinabove or the composition such as described hereinabove, for its use as a drug, as a medical device, as a dermatological agent, as a cosmetic agent, or as a nutraceutical, for human or animal use, advantageously in the prevention and/or the treatment of connective tissue disorders such as arthrosis, articular pathologies such as rhumatisms, parodontal disorders such as gingivitis or parodontitis, or even in the prevention and/or the treatment of disorders of the dermis and/or of the hypodermis such as cutaneous ageing, stretch marks and cellulite, or even disorders of the epidermal barrier such as cutaneous inflammations, atopic eczema and irritative and/or inflammatory dermatitis.

In particular, the aim of the present invention is an avocado unsaponifiable rich in aliphatic furans or a concentrate of avocado oil enriched in unsaponifiable, said unsaponifiable or said concentrate being able to be obtained from the avocado oil according to the invention, for its use as a drug, advantageously in the prevention and/or the treatment of connective tissue disorders such as arthrosis, articular pathologies such as rhumatisms, or parodontal disorders, such as gingivitis or parodontitis.

In addition, medical device according to the invention means any instrument, apparatus, equipment, material, product, with the exception of products of human origin, or other article alone or in association, designed by the manufacturer to be used in humans for medical purposes and whereof the preferred principal action is not obtained by pharmacological or immunological means or by metabolism, but the function of which can be assisted by such means.

Advantageously, the compositions according to the invention are adapted to oral administration, such as a pharmaceutical composition or a drug, a food supplement or a nutraceutical composition.

According to a variant, the compositions according to the invention are adapted to topical administration and include especially creams, emulsions, milks, pomades, lotions, oils, aqueous or hydro-alcoholic or glycolic solutions, powders, patches, sprays, shampoos, enamels or any other product for external application.

The following examples are given to illustrate the invention:

EXAMPLE 1

Extraction of Oil from Soft Avocado Fruits: Influence of Granulometry During Grinding (1) and of Water Adding (3) Before Pressing (4) in Avocados Previously Dried 3 kg of soft avocados from Kenya, of 18 calibre, of the hass variety and of hardness measured by means of a penetrometer of between 0.1 and 0.3 kg/cm$^2$, are ground in a RETSCH knife grinder of SM 100 type equipped according to the preferred granulometry with a sieve with apertures of 20 mm, 10 mm or 1 mm.

The ground product is deposited onto a tray of 0.158 m$^2$, at a thickness of 2 cm.

The tray is then placed into a ventilated heat chamber and drying is conducted with air circulation at 80±5° C. for 72 hours.

The dried ground product is recovered and ground for homogenisation on the RETSCH knife grinder of SM 100 type equipped with a sieve with apertures of 20 mm.

Residual humidity is measured by means of a thermogravimetric method by IR drying.

After the assays, the ground product is then hydrated or not by vaporisation of a quantity of adapted purified water and by homogenisation in a planetary mixer, just before being introduced to the press for extraction of the oil.

The avocado oil is then extracted by mechanical pressure on a laboratory screw press of Komet type.

The quantities of oil and oil cake are determined by weighing for each assay and the extraction yield is calculated by the following formula:

$$\text{Mass of oil recovered} \times 100 / (\text{Mass of oil recovered} + \text{mass of oil cake})$$

Physico-chemical and chromatographic analysis of oils compares the compositions of the different oils obtained.

| Assay No. | Screen mesh mm | RH after drying % | % added water % | Extraction yield % | Content of acetogenins m/m | Content of unsaponifiable m/m | AI mg KOH/g |
|---|---|---|---|---|---|---|---|
| 1 | 1 | 6.0 | 0 | 17.2 | 3.24 | 3.99 | 3.1 |
| 2 | 10 | 1.5 | 0 | 16.6 | 3.67 | 4.40 | 0.9 |
| 3 | 10 | 1.5 | 3.6 | 43.3 | 3.71 | 4.30 | 1.7 |
| 4 | 20 | 1.4 | 3.9 | 41.6 | 3.56 | 4.43 | 1.4 |

Assay No. 1 reveals that a particle size corresponding to grinding with a screen size of 1 mm of does not produce after 72 h of drying residual humidity (RH) under 5%, effectively compromising the storage quality of dried avocados and resulting in a very low pressing yield and an oil more weakly dosed in acetogenins and unsaponifiable. It also results in an acid value (AI) greater than 3 of the avocado oil obtained.

Pressing assays No. 2 and 3 reveal that water adding in fruits dried before pressing reaches a high pressing yield in the case of assay No. 3, compared to assay No. 2 in which no water adding operation was employed.

Assays 3 and 4, by comparison to assay 1, reveal the benefit of a particle size of between 10 and 20 mm on the composition of the oil, especially on its content of acetogenins and unsaponifiable.

EXAMPLE 2

Extraction of Oil from Soft Avocado Fruits Including Especially a Separate Grinding Step (1) of the Different Parts of the Avocado and Influence of Water Adding (3) Before Pressing (4) in Dried Avocados (2)

3 kg of soft avocados from Kenya, of calibre 18, of hass variety and hardness measured by means of a penetrometer, of between 0.1 and 0.3 kg/cm$^2$, are dekerneled and depulped, then the two parts (both pulp and kernel+skin) are ground in a RETSCH knife grinder of SM 100 type equipped according to the preferred granulometry with a sieve with apertures of 10 mm.

Part of the ground pulp is remixed with its corresponding part of kernel+skin ground in the original proportions (assay No. 7). Another part of the pulp is dried alone (assay No. 6).

The different ground products are spread onto trays at a thickness of 2 cm. The tray is then placed into a ventilated heat chamber and drying is carried out with air circulation at 80±5° C. for 72 hours.

The dried ground products are recovered and ground for homogenisation on the RETSCH knife grinder of SM 100 type equipped with a sieve with apertures of 20 mm.

The residual humidity is measured by means of a thermogravimetric method by IR drying.

Following the assays, the ground product is then hydrated or not by vaporisation of a quantity of adapted purified water and by homogenisation in a planetary mixer, just before being introduced to the press for extraction of the oil.

The avocado oil is then extracted by mechanical pressure on a laboratory screw press of Komet type.

The quantities of oil and oil cake are determined by weighing for each assay and the extraction yield is calculated by the following formula:

Mass of oil recovered×100/(Mass of oil recovered+ mass of oil cake).

Physico-chemical and chromatographic analysis of the oils compares the compositions of the different oils obtained.

| Assay No. | Part | Screen mesh mm | RH after drying % | % added water % | Extraction yield % | Content of acetogenins m/m | Content of unsaponifiable m/m | AI mg KOH/g |
|---|---|---|---|---|---|---|---|---|
| 5 | Whole avocado | 10 | 1.5 | 3.6 | 43.3 | 3.71 | 4.30 | 1.7 |
| 6 | Only pulp | 10 | 5.7 | 0 | 58.2 | 2.89 | 3.99 | 3.3 |
| 7 | Pulp, kernel and skin remixed | 10 | 1.6 | 1.9 | 43.7 | 3.67 | 4.40 | 1.0 |

Assay No. 6 reveals that grinding of just the pulp, even with a mesh of 10 mm, fails to produce residual humidity (RH) under 5% after 72 h of drying, compromising the storage quality of the dried avocados and resulting in an oil more weakly dosed in acetogenins and unsaponifiable. It also results in an acid value (AI) greater than 3 of the avocado oil obtained.

Assays No. 5 and 7 comparatively reveal that grinding separate of the different parts of the avocado, then homogenisation of the ground product mixture before drying on the one hand, and grinding of the avocado in its entirety on the other hand yield similar results in terms of pressing yield after water adding of the dried fruits and in terms of composition of the oil obtained.

Additional assays using increasing percentages of water during water adding of the mixture pulp, skin and kernel dried reveal the role of this key step of the process to obtain a maximal extraction yield.

| Assay No. | Part | Screen size mm | RH after drying % | % water added % | Extraction yield % |
|---|---|---|---|---|---|
| 8 | Pulp, kernel and skin remixed | 10 | 1.6 | 0 | 9.1 |
| 9 | | | | 1.9 | 43.7 |
| 10 | | | | 4.4 | 42.2 |

Assays No. 9 and 10 reveal that water adding of the dried fruits before pressing achieves a high pressing yield, compared to assay No. 8 in which no water adding operation has been employed.

COMPARATIVE EXAMPLE 3

Extraction of Oil by Centrifuging from Whole Soft Avocado Fruits 100 kg of soft avocados of Mexican origin, of hass variety, are processed on a refiner of rotating screen type to separate the skin and the kernel, and the pulp is then processed as per the following operations:

Water is added to the pulp obtained and the mixture is heated at 80° C.,

The mixture then undergoes centrifuging to separate the liquid part comprising oil and water from the solid part, The oil is then separated from the aqueous phase by a novel centrifuging step, The resulting oil undergoes the final filtration phase before being packaged.

Physico-chemical and chromatographic analysis of this oil has given the following results:

Acid value: 2.7 mg KOH/g,
Content of aliphatic acetogenins and/or their derivatives: 0.55 g/100 g,
Content of sterols: 0.52 g/100 g,
Content of unsaponifiable: 1.19 g/100 g.

The oil obtained has a satisfactory acid value, but shows a very low content of aliphatic acetogenins and/or their derivatives, which demonstrates the inefficacy of the process by centrifuging to extract the polar compounds from the unsaponifiable.

The invention claimed is:

1. A process comprising:
grinding whole soft avocados,
drying said whole soft ground avocados at a temperature between 60 and 150° C. to obtain a residual humidity less than or equal to 5%,
adding 1 to 5% of water or water vapour relative to the mass of ground dry avocados, and then
applying mechanical pressure to the mass of ground dry whole soft avocados to obtain avocado oil containing at least 3% of unsaponifiable mass relative to the total mass of the oil, said unsaponifiable containing aliphatic acetogenins and/or their derivatives, in which the content of aliphatic acetogenins and/or their derivatives of the oil is at least 2% m/m, the soft avocados having a penetration resistance force in the flesh less than or equal to 3 kg/cm$^2$, said penetration resistance force being measured by means of a penetrometer.

2. The process as claimed in claim 1, wherein the soft avocados have a penetration resistance force in the flesh less than or equal to 2 kg/cm$^2$, said penetration resistance force being measured by means of a penetrometer.

3. The process as claimed in claim 1, wherein the unsaponifiable content of the oil is at least 5% m/m and/or the content of aliphatic acetogenins and/or their derivatives of the oil is at least 3% m/m.

4. The process as claimed in claim 1, wherein the oil has an acid value less than or equal to 5 mgKOH/g.

5. The process as claimed in claim 1, wherein the unsaponifiable of the oil contains sterols and the sterol content of the oil is at least 0.5% m/m.

6. The process as claimed in claim 1, wherein the aliphatic acetogenins and their derivatives are selected from the group consisting of fatty polyhydroxy alcohols and their acetylated derivatives, 1,2-dihydroxy-4-oxo-aliphatic alcohols and their acetylated derivatives of persin type, and aliphatic furans, as well as their mixtures.

7. A process for obtaining an avocado oil from whole soft avocados, said oil containing at least 3% by unsaponifiable mass relative to the total mass of the oil, in which said unsaponifiable contains aliphatic acetogenins and/or their derivatives, comprising the following successive steps:
(1) Grinding of the soft avocados resulting in obtaining a ground product granulometry of between 2 and 20 mm, in particular between 2 and 10 mm,
(2) Drying of the ground product at a temperature between 60 and 150° C., to obtain a residual humidity less than or equal to 5%,
(3) Water adding in dried avocados by addition of 1 to 5% of water or steam relative to the mass of ground dry avocados, then
(4) Extraction of the oil by mechanical pressure.

8. The process for obtaining avocado oil as claimed in claim 7, wherein the grinding (1) is carried out on the whole avocados constituted by the skin, the pulp and the kernel, by shredding of the skin, grinding of the kernel and blending of the mixture to obtain a homogeneous dispersion of the ground product, by means of a grinder of serrated knives or rollers type.

9. The process for obtaining an avocado oil as claimed in claim 7, wherein the grinding (1) is carried out by:
Separation of the kernel and of the skin from the pulp of the avocados,
Grinding of the different parts of the soft avocados, then
Blending of the different ground parts to obtain a homogeneous dispersion.

10. The process for obtaining an avocado oil as claimed in claim 7, wherein following grinding (1) and prior to drying (2), conditioning of the ground product is carried out to boost the surface of the ground product to be dried, by spreading in a thin layer, to result in a film of a thickness of between 0.5 and 5 cm, or by shaping to optimise the evaporation surface of the extrusion type or passing through a die.

11. The process for obtaining an avocado oil as claimed in claim 7, wherein the drying (2) of the ground product is carried out for 8 to 78 h.

12. Oil of avocado obtained by the process as claimed in claim 7, wherein the oil contains at least 3% of unsaponifiable mass, relative to the total mass of the oil and at least 2% by mass of aliphatic acetogenins and/or of their derivatives, relative to the total mass of the oil, said aliphatic acetogenins and their derivatives being fatty polyhydroxy alcohols and their acetylated derivatives, and/or 1,2-dihydroxy-4-oxo-aliphatic alcohols and their acetylated derivatives of persin type, and/or aliphatic furans.

13. The avocado oil as claimed in claim 12, containing at least 5% of unsaponifiable mass, relative to the total mass of the oil, and/or containing at least 3% by mass of aliphatic acetogenins and/or of their derivatives, relative to the total mass of the oil.

14. The avocado oil as claimed in claim 12, wherein the oil has an acid value less than or equal to 5 mgKOH/g.

15. The avocado oil as claimed in claim 12, wherein said unsaponifiable contains sterols and said oil contains at least 0.5% by mass of sterols, relative to the total mass of the oil.

16. A process comprising:
preparing a concentrate of avocado oil enriched in unsaponifiable by cold crystallisation or by molecular distillation of the avocado oil as claimed in claim 12.

17. A process comprising:
preparing an avocado unsaponifiable rich in aliphatic furans by thermal treatment at a temperature between 80 and 150° C. of the avocado oil as claimed in claim 12 or a concentrate of avocado oil enriched in unsaponifiable obtained from the avocado oil, followed by a saponification and extraction step of the unsaponifiable.

18. The process as claimed in claim 2, wherein the soft avocados have a penetration resistance force in the flesh less than or equal to 1 kg/cm$^2$, said penetration resistance force being measured by means of a penetrometer.

19. The process for obtaining avocado oil as claimed in claim 7, wherein the drying (2) of the ground product is carried out at a temperature between 70 and 100° C.

20. The process for obtaining an avocado oil as claimed in claim 10, wherein following grinding (1) and prior to drying (2), conditioning of the ground product is carried out to boost the surface of the ground product to be dried, by spreading in a thin layer, to result in a film of a thickness of between 1 and 2 cm, or by shaping to optimise the evaporation surface of the extrusion type or passing through a die.

21. The process for obtaining an avocado oil as claimed in claim 11, wherein the drying (2) of the ground product is carried out for 10 to 24 h.

\* \* \* \* \*